US010016355B2

(12) United States Patent
Pineau

(10) Patent No.: US 10,016,355 B2
(45) Date of Patent: Jul. 10, 2018

(54) COSMETIC COMPOSITION CONTAINING COPA

(75) Inventor: Quentin Pineau, Evreux (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 13/807,805

(22) PCT Filed: Jun. 29, 2011

(86) PCT No.: PCT/FR2011/051510
§ 371 (c)(1),
(2), (4) Date: Feb. 22, 2013

(87) PCT Pub. No.: WO2012/001299
PCT Pub. Date: Jan. 5, 2012

(65) Prior Publication Data
US 2013/0142747 A1    Jun. 6, 2013

(30) Foreign Application Priority Data
Jul. 1, 2010 (FR) ..................................... 10 02790

(51) Int. Cl.
*A61K 8/88* (2006.01)
*A61Q 1/14* (2006.01)
*A61Q 1/10* (2006.01)
*A61Q 19/00* (2006.01)

(52) U.S. Cl.
CPC ............... *A61K 8/88* (2013.01); *A61Q 19/00* (2013.01); *A61Q 1/10* (2013.01); *A61Q 1/14* (2013.01)

(58) Field of Classification Search
None
See application file for complete search history.

(56) References Cited

U.S. PATENT DOCUMENTS

| 4,097,589 A | 6/1978 | Shansky |
| 5,516,815 A * | 5/1996 | Buehler ............... D01F 6/88 523/124 |
| 7,700,124 B2 | 4/2010 | Loyen et al. |
| 2006/0115504 A1 | 6/2006 | Loyen et al. |
| 2007/0055044 A1 * | 3/2007 | Simon ............... A41D 27/06 528/310 |
| 2009/0075081 A1 * | 3/2009 | Ouvrard et al. ............ 428/402 |
| 2009/0304757 A1 * | 12/2009 | Herve et al. ............... 424/401 |
| 2010/0215701 A1 | 8/2010 | Loyen |

FOREIGN PATENT DOCUMENTS

| EP | 1661546 A1 | 5/2006 |
| FR | 2939802 A1 | 6/2010 |
| WO | 2008145889 A2 | 12/2008 |

OTHER PUBLICATIONS

ORGASOL Product Brochure, http://www.orgasolpowders.com/en/markets-and-applications/.*
English Translation of Abstract for FR2939802A1 dated Jun. 18, 2010.
International Search Report dated Dec. 15, 2011.

* cited by examiner

*Primary Examiner* — Robert A Wax
*Assistant Examiner* — Randeep Singh
(74) *Attorney, Agent, or Firm* — Millen, White, Zelano and Branigan, P.C.

(57) ABSTRACT

The invention relates to a composition containing between 0.1 and 30 wt.-% copolyamide (COPA) and between 70 and 99.9 wt.-% of a medium acceptable for cosmetic, perfume and/or pharmaceutical use. In particular, the invention relates to a method for incorporating a copolyamide into a cosmetic, perfume and/or pharmaceutical medium. The invention also relates to the use of a copolyamide (COPA) for the production of a cosmetic, pharmaceutical or perfume product, said COPA being incorporated in the form of a composition in accordance with the invention.

16 Claims, No Drawings

COSMETIC COMPOSITION CONTAINING COPA

FIELD OF THE INVENTION

A subject matter of the present invention is a cosmetic composition comprising a thermoplastic polymer, in particular a copolyamide (hereafter COPA).

The present invention relates in particular to the use of these COPAs in cosmetic, pharmaceutical or perfumery products and to the cosmetic, pharmaceutical or perfumery compositions comprising at least one COPA.

PRIOR ART

Thermoplastic polymers intended for cosmetic or medical use are generally provided in the powder form. Consequently, the formulation with these powders generally requires intermediate stages of grinding indeed even of sieving, in the form of a fine powder with a D50 generally of less than 10 or 20 µm, and of preliminary dispersion of this powder in a liquid in order for the texture of the final product incorporating the powder to exhibit perfect homogeneity and uniform appearance. Furthermore, the high volatility of the fine powders means that their use in formulation requires many precautions. It is difficult in particular for formulators to exactly and reproducibly quantify the powder content of the formulas.

Among thermoplastic polymers, copolyamides (hereinafter COPAs) are known as adhesives of the hot melt adhesive (or HMA) type, that is to say they are deposited in a molten state of the surfaces to be adhesively bonded, the adhesion being subsequently obtained by cooling, by the return of the copolyamides to the solid state. The melting point of these COPAs is within the range from 80 to 190° C., preferably from 100 to 130° C. The composition of monomers and the ratio by weight between the monomers determine in particular the properties of adhesion to various supports and the chemical resistance of these COPAs. Their properties have already been made use of in the textile industry, in the manufacture of films, filaments, nets or meshes, of varnishes, of paints or of inks, and for coating materials, in particular with fine COPA powders. On the other hand, these properties of the COPAs have never been made use of in the cosmetics field, where the challenges faced by formulators in terms of texture and feel are increasingly demanding and varied.

It is thus an aim of the present invention to provide ready-for-use compositions comprising COPA which facilitate the use of the COPA by the formulators by being directly usable (by simple incorporation) in cosmetic formulations, for example in order to confer a particular texture thereon. Thus, the formulator no longer needs to adjust beforehand the form of the COPAs sold commercially in the powder or granule form. Furthermore, the COPA contents of the formulations can be easily quantified and reproduced.

An aim of the present invention is in particular to provide a simple process (comprising the fewest possible stages) for the manufacture of such ready-for-use COPA compositions.

Surprisingly, the Applicant Company has also shown that the use of copolyamides makes it possible to manufacture such cosmetic compositions having innovative textures and properties.

DETAILED DESCRIPTION OF THE INVENTION

The subject matter of the present invention is thus a composition comprising:

from 0.1 to 30% by weight of copolyamide (COPA), and
from 70 to 99.9% by weight of a medium acceptable in cosmetics, in perfumery and/or in pharmaceuticals.

COPA:

The "copolyamides", abbreviated to "COPAs", comprise at least two distinct repeat units, these distinct units being formed from at least two different monomers. The copolyamides are thus prepared from two or more comonomers chosen from an amino acid, a lactam and/or a dicarboxylic acid with a diamine.

The term "monomer" in the present description of the copolyamides should be taken to mean "repeat unit". This is because the case where a repeat unit of the PA is composed of a combination of a diacid with a diamine is particular. It is considered that it is the combination of a diamine and of a diacid, that is to say the diamine.diacid pair (in equimolar amounts), which corresponds to the monomer. This is explained by the fact that individually the diacid or the diamine is only a structural unit which is not sufficient in itself alone to be polymerized.

The term "copolyamide" (abbreviated to COPA), is understood to mean the polymerization products of at least two different monomers chosen from:

monomers of amino acid or aminocarboxylic acid type and preferably $\alpha,\omega$-aminocarboxylic acids;

monomers of lactam type which have from 3 to 18 carbon atoms on the main ring and which can be substituted;

monomers of "diamine.diacid" type resulting from the reaction between an aliphatic diamine having from 4 to 36 carbon atoms and a dicarboxylic acid having from 4 to 36 carbon atoms; and their mixtures, with monomers comprising a different carbon number in the case of mixtures between a monomer of amino acid type and a monomer of lactam type.

Monomers of Amino Acid Type:

Mention may be made, as examples of $\alpha,\omega$-amino acids, of those having from 4 to 18 carbon atoms, such as aminocaproic, 7-aminoheptanoic, 11-aminoundecanoic, 11-(n-heptylamino)undecanoic and 12-aminododecanoic acids.

Monomers of Lactam Type:

Mention may be made, as examples of lactams, of those which have from 3 to 18 carbon atoms on the main ring and which can be substituted. Mention may be made, for example, of β,β-dimethylpropiolactam, α,α-dimethylpropiolactam, amylolactam, caprolactam, also known as lactam 6, capryllactam, also known as lactam 8, oenantholactam, 2-pyrrolidone and lauryllactam, also known as lactam 12.

Monomers of "diamine.diacid" Type:

Mention may be made, as examples of dicarboxylic acid, of acids having from 4 to 36 carbon atoms. Mention may be made, for example, of adipic acid, sebacic acid, azelaic acid, suberic acid, isophthalic acid, butanedioic acid, 1,4-cyclohexanedicarboxylic acid, terephthalic acid, the sodium or lithium salt of sulfoisophthalic acid, dimerized fatty acids (these dimerized fatty acids have a dimer content of at least 98% and are preferably hydrogenated) and dodecanedioic acid HOOC—$(CH_2)_{10}$—COOH.

Mention may be made, as example of diamine, of aliphatic diamines having from 4 to 18 atoms, which can be arylic and/or saturated cyclic. Mention may be made, as examples, of hexamethylenediamine, piperazine (abbreviated to "Pip"), tetramethylenediamine, octamethylenediamine, decamethylenediamine, dodecamethylenediamine, 1,5-diaminohexane, 2,2,4-trimethyl-1,6-diaminohexane, polyoldiamines, isophoronediamine (IPD), methylpentamethylenediamine (MPDM), bis(aminocyclohexyl)methane (BACM), bis(3-methyl-4-aminocyclohexyl)methane (BMACM), meta-xylylenediamine, bis(p-aminocyclohexyl) methane and trimethylhexamethylenediamine.

Mention may be made, as examples of monomers of "diamine.diacid" type, of those resulting from the condensation of hexamethylenediamine with a $C_6$ to $C_{36}$ diacid, in particular the monomers: 6.6, 6.10, 6.11, 6.12, 6.14 and 6.18. Mention may be made of the monomers resulting from the condensation of decanediamine with a $C_6$ to $C_{36}$ diacid, in particular the monomers: 10.10, 10.12, 10.14 and 10.18.

Mention may be made, as examples of copolyamides formed from different types of monomers described above, of the copolyamides resulting from the condensation of at least two α,ω-aminocarboxylic acids or of two lactams or of one lactam and of one α,ω-aminocarboxylic acid. Mention may also be made of the copolyamides resulting from the condensation of at least one α,ω-aminocarboxylic acid (or one lactam), at least one diamine and at least one dicarboxylic acid. Mention may also be made of the copolyamides resulting from the condensation of an aliphatic diamine with an aliphatic dicarboxylic acid and of at least one other monomer chosen from aliphatic diamines other than the preceding one and aliphatic diacids other than the preceding one.

Mention may be made, as examples of copolyamides, of copolymers of caprolactam and lauryllactam (PA 6/12), copolymers of caprolactam, hexamethylenediamine and adipic acid (PA 6/6.6), copolymers of caprolactam, lauryllactam, hexamethylenediamine and adipic acid (PA 6/12/6.6), copolymers of caprolactam, hexamethylenediamine and azelaic acid, 11-amino undecanoic acid and lauryllactam (PA 6/6.9/11/12), copolymers of caprolactam, adipic acid and hexamethylenediamine, 11-aminounecanoic acid and lauryllactam (PA 6/6.6/11/12), copolymers of hexamethylenediamine, azelaic acid and lauryllactam (PA 6.9/12), copolymers of 2-pyrrolidone and caprolactam (PA 4/6), copolymers of 2-pyrrolidone and lauryllactam (PA 4/12), copolymers of caprolactam and 11-aminoundecanoic acid (PA 6/11), copolymers of lauryllactam and capryllactam (PA 12/8), copolymers of 11-aminoundecanoic acid and 2-pyrrolidone (PA 11/4), copolymers of capryllactam and caprolactam (PA 8/6), copolymers of capryllactam and 2-pyrrolidone (PA 8.4), copolymers of lauryllactam and capryllactam (PA 12/8) or copolymers of lauryllactam and 11-aminoundecanoic acid (PA 12/11).

Advantageously, the COPA used in the composition according to the invention is obtained at least partially from bioresourced starting materials.

The term "starting materials of renewable origin" or "bioresourced starting materials" is understood to mean materials which comprise bioresourced carbon or carbon of renewable origin. Specifically, unlike the materials resulting from fossil materials, the materials composed from renewable starting materials comprise $^{14}C$. The "content of carbon of renewable origin" or "content of bioresourced carbon" is determined by application of the standards ASTM D 6866 (ASTM D 6866-06) and ASTM D 7026 (ASTM D 7026-04). By way of example, the COPAs based on polyamide 11 originate at least in part from bioresourced starting materials and exhibit a content of bioresourced carbon of at least 1%, which corresponds to a $^{12}C/^{14}C$ isotopic ratio of at least $1.2 \times 10^{-14}$. Preferably, the COPAs according to the invention comprise at least 50% by weight of bioresourced carbon with regard to the total weight of carbon, which corresponds to a $^{12}C/^{14}C$ isotopic ratio of at least $0.6 \times 10^{-12}$. This content is advantageously higher, in particular up to 100%, which corresponds to a $^{12}C/^{14}C$ isotopic ratio of $1.2 \times 10^{-12}$, in the case of COPAs resulting entirely from starting materials of renewable origin.

Mention may be made, as examples of amino acids of renewable origin, of: 11-aminoundecanoic acid, for example produced from castor oil, 12-aminododecanoic acid, for example produced from castor oil, 10-aminodecanoic acid, for example produced from decylenic acid obtained by metathesis of oleic acid, or 9-aminononanoic acid, for example produced from oleic acid.

Mention may be made, as examples of diacids of renewable origin, as a function of the number x of carbons in the molecule ($C_x$), of:

$C_4$: succinic acid, for example from glucose;
$C_6$: adipic acid, for example from glucose;
$C_7$: heptanedioic acid from castor oil;
$C_9$: azelaic acid, for example from oleic acid (ozonolysis);
$C_{10}$: sebacic acid, for example from castor oil;
$C_{11}$: undecanedioic acid from castor oil;
$C_{12}$: dodecanedioic acid, for example from biofermentation of dodecanoic acid=lauric acid (rich oil: palm kernel oil and coconut oil);
$C_{13}$: brassylic acid, for example from erucic acid (ozonolysis) which is found in rape;
$C_{14}$: tetradecanedioic acid, for example by biofermentation of myristic acid (rich oil: palm kernel oil and coconut oil);
$C_{16}$: hexadecanedioic acid, for example by biofermentation of palmitic acid (mainly palm oil);
$C_{18}$: octadecanedioic acid, for example obtained by biofermentation of stearic acid (a small amount in all vegetable oils but predominant in animal fats);
$C_{20}$: eicosanedioic acid, for example obtained by biofermentation of arachidic acid (predominantly in rapeseed oil);
$C_{22}$: docosanedioic acid, for example obtained by metathesis of undecylenic acid (castor oil);
$C_{36}$: fatty acid dimer resulting from softwood byproducts transformed by the kraft process.

Mention may be made, as examples of diamines of renewable origin, as a function of the number x of carbons in the molecule ($C_x$):

$C_4$: butanediamine obtained by amination of succinic acid;
$C_5$: pentamethylenediamine (from lysine); and so on for the diamines obtained by amination of the diacids of renewable origin seen above.

The term "copolyamide of completely renewable origin" is understood to mean the copolyamides resulting from the polymerization of various monomers (renewable, non-renewable, or mixed), such as those mentioned above. This is the case, for example, of COPA 6.6/10.10 in which the monomer "6.6" is of non-renewable origin whereas the monomer "10.10" is of renewable origin.

The term "copolyamide of completely renewable origin participating in the composition of the invention" is understood to mean the copolyamides resulting from the polymerization of various monomers, such as those mentioned above, such as, for example, the following copolyamides: PA 11/10.10, PA 11/10.36, PA 10.10/10.36, the 11-aminoundecanoic/11-(n-heptylamino)undecanoic copolyamide and the like.

Use is made advantageously of one or more of the following copolyamides in the composition or the process of the present invention:

PA 6/6.6/12, the ratios by weight of corresponding monomers of which can be (as a percentage): 40/20/40, 35/20/45, 45/35/20, 30/30/40, 22/18/60 or 40/25/35;
PA 6/6.6/12, the ratios by weight of corresponding monomers of which can be, for example (as a percentage): 30/15/10/45, 30/20/20/30 or 15/25/25/35;
PA 6/12 with a ratio by weight of 70/30;
PA 6.9/12 with a ratio by weight of 30/70;
PA Pip.9/Pip.12/11 with a ratio by weight of 15/70/15;
PA 6/IPD.6/12 with a ratio by weight of 20/15/65;
PA IPD.9/12 with a ratio by weight of 20/80;
PA 6/6.12/12 with a ratio by weight of 30/30/40;
PA 6/Pip.12/12 with a ratio by weight of 30/20/50;
PA 6/6.12/11/PEG.12 with a ratio by weight of 25/21/25/30;
PA 6/6.6/6/10/6.1 with a ratio by weight of 40/10/40/10;
PA 6.10/Pip.10/Pip.12 with a ratio by weight of 20/40/40;
PA 6/11/12 with a ratio by weight of 10/36/54;
PA Pip.12/12 with a ratio by weight of 35/65;
PA IPD.10/12 with a ratio by weight of 80/20;
PA Pip.10/12 with a ratio by weight of 72/28;
PA 6/11 with a ratio by weight of 50/50;
PA Pip.10/11/Pip.9 with a ratio by weight of 65/30/5;
PA 6/6.6/6.10 with a ratio by weight of 35/30/35.

Mention may in particular be made, as examples of copolyamides, of those sold under the "Platamid®" and Platamid Rnew® names by Arkema.

The term "medium acceptable in cosmetics, perfumery or pharmaceuticals" is understood to mean, within the meaning of the invention, any product which does not cause irritation or reaction on the skin, keratinous fibers (eyelashes, hair) or nails.

Advantageously, said medium comprises at least one component chosen from water, alcohols, alcoholic solutions, lipid compounds, glucide compounds, hydrocarbons, synthetic polymers, natural polymers and/or plant extracts.

Advantageously, the composition according to the invention has at least one of the following forms: dispersion, solution, emulsion, micro emulsion, nanoemulsion, dry emulsion, suspension, aerosol, gel, compact gel, gum, plastic gum, paste, foam, cream, powder, loose powder, compact powder, expanded powder, butter, film, elastic film and their mixtures.

Advantageously, said medium comprise an aqueous phase comprising at least 50% water. The water can be softened water, demineralized water, and/or sterilized water, according to its degree of purification, thermal water and the like.

The aqueous phase can additionally comprise alcohols, the number of carbons of the carbon chain of which does not exceed 6 and which are water-soluble, such as ethanol or isopropanol. Alcoholic solutions obtained by simple mixing of these alcohols with water can also be used in the aqueous phase; as well as glycols, such as ethylene glycol or propylene glycol; polyols, such as glycerol or glycerine, sorbitol or sorbitol syrup.

Polyoxyethylene glycols (PEG) can also be used as solvents in said aqueous phase. Carboxyvinyl polymers (carbomers or Carbopol), cyanoacrylic polymers; glucide compounds, such as polysaccharides extracted from algae (alginates, carrageenates), wood (cellulose and its derivatives), tree sap (gum arabic, gum tragacanth), seeds or pips (pectin, guar gum, locust bean gum, starch) or leaves (aloe gel); glycoproteins or proteoglycans; glucide esters and ethers can also participate in the composition of the aqueous phase, in particular as thickeners or gelling agents for the aqueous phase.

Preservatives, hydrophilic emulsifiers, dyes, humectants, gelling agents, hydrophilic active agents or any other hydrophilic cosmetic agents can participate in the composition of said aqueous or hydrophilic phase.

Advantageously, said medium comprises an oily phase comprising at least 50% of organic solvent chosen from fatty esters, fatty alcohols, fatty acids and their mixtures.

Fatty alcohols within the meaning of the invention are alcohols, the carbon chain of which comprises at least 7 carbons, preferably from 7 to 10 carbons, so that they are liquid at ambient temperature. They are insoluble in water but the presence of hydroxyl confers on them a weak affinity for water. Mention may be made in particular of benzylic alcohol which acts as solvent and preservative.

Fatty acids within the meaning of the invention are organic acids which occur in lipids. Their carbon chain is more or less lengthy (from $C_4$ to $C_{30}$) and they can be saturated or unsaturated. Saturated fatty acids are solid at ambient temperature (25° C.), except for $C_4$ and $C_6$ acids. Unsaturated fatty acids are liquid. Mention may be made, by way of example, of lauric acid, stearic acid or oleic acid.

Fatty esters result either from the combination of a fatty acid with a short-chain alcohol (for example isopropyl palmitate or myristate, which form liquid fatty esters), or from the combination of a fatty acid with a fatty alcohol (for example isostearyl isostearate), or from the combination of a short-chain acid with a fatty alcohol having a more or less lengthy chain (for example benzoic acid with a $C_{13}$-$C_{15}$ fatty alcohol, forming fatty alcohol benzoates).

Other lipid compounds can occur in said oily phase, such as vegetable oils, for example jojoba oil, castor oil, peanut oil, sunflower oil, borage oil or coconut oil; animal oils; it being possible for these oils to be or not to be chemically modified; synthetic oils, such as synthetic mono-, di-, and triglycerides, for example caprylic/capric triglycerides; non-saponifiable products, in particular from avocado, soya, corn or shea; butters, in particular shea, coconut or cocoa butter; waxes with a melting point of greater than 50° C. of vegetable origin (carnauba wax, candelilla wax) or animal origin (beeswax, propolis); or phospholipids, in particular soybean lecithin.

Said oily phase may also include mineral hydrocarbons: mineral oils, petrolatums, paraffins or isoparaffins; or silicones, such as silicone oils, for example dimethicone or phenyl methicone, volatile silicones, such as cyclomethicones, or emulsifying silicones.

The oily phase can also comprise silicas, silicates, in particular aluminum and/or magnesium silicate, clay, kaolin, montmorillonite, bentone, bentonite or hectorite, which thicken the oily phase.

Antioxidants, pigments, fillers such as talc, nylon or silica, lipophilic active agents and any other lipophilic cosmetic agent can also participate in the composition of said oily phase.

Advantageously, said medium additionally comprises from 0.1 to 30% by weight of surfactant with regard to the total weight of COPA.

The term "surfactant" is understood to mean, within the meaning of the invention:
surfactants of synthetic origin which are themselves divided into two groups, ionic surfactants (anionic surfactants, such as sodium lauryl sulfate or fatty acid salts, cationic surfactants, such as stearylammonium chloride, or amphoteric surfactants such as betaine derivatives) and nonionic surfactants with an HLB within the range from 0 to 20, for example sorbitan esters (Span, Tween) and polyoxy-ethylenated fatty alcohols; and surfactants of natural origin, such as cholesterol, lecithin, saponin, and proteins such as casein.

Preferably, the surfactant according to the invention is chosen from anionic surfactants and nonionic surfactants. The surfactant is advantageously chosen from salts of alkyl ether sulfate and of polyoxyalkylene, dialkyl sulfosuccinate salts, fatty acid salts and copolyamides of ethylene oxide/propylene oxide, and their mixtures.

Preferably, the composition according to the invention comprises:

from 0.1 to 30% of COPA,
from 40 to 99.9% of oily phase and/or of aqueous phase,
from 0 to 30% of surfactant, preferably from 0.1 to 20% of surfactant, with regard to the total weight of the composition.

Advantageously, the composition according to the invention additionally comprises a lipophilic or hydrophilic thickener or gelling agent, such as those described above.

According to a preferred embodiment of the invention, the composition forms a dispersion of COPA dissolved in an oily phase dispersed in an aqueous phase in the presence of a surfactant.

According to another advantageous embodiment of the invention, the composition forms a dispersion of COPA dissolved in an aqueous phase dispersed in an oily phase in the presence of a surfactant.

Another subject matter of the present invention is a method for the incorporation of a copolyamide in a cosmetic, perfumery and/or pharmaceutical medium, said method comprising at least one stage chosen from: mixing, dispersing, homogenizing, high pressure homogenizing, dissolving, diluting, gelling, thickening, emulsifying, refining, forming a paste, heat treating, drying, lyophilizing, baking, extruding, grinding, granulating, atomizing, filtering and the successive or simultaneous mixtures of several of these stages.

Advantageously, said method comprises the stages of:
direct or gradual addition, preferably with stirring, within the range from 100 to 20 000 rev/min, of copolyamide (COPA) to a medium acceptable in cosmetics, in perfumery and/or in pharmaceuticals, the COPA/medium ratio by weight being within the range from 40/60 to 1/99, the limits of the range being included; and
heating said mixture at a temperature within the range from 40 to 190° C., preferably in the range from 60 to 180° C., preferably from 70 to 130° C., preferably under a pressure within the range from 1 to 100 bar, for a period of time within the range from 5 to 120 minutes, preferably from 5 to 60 minutes and preferably from 10 to 30 minutes; the addition and heating stages being simultaneous or successive, taken in this order or in the reverse order.

Preferably, the method according to the invention comprises the addition of from 0.1 to 30% of copolyamide (COPA) to from 70 to 99.9% of a medium acceptable in cosmetics and/or in perfumery, the mixture obtained representing 100%.

Preferably, the COPA used in the method of the invention is in the form of a powder with a D50 within the range from 1 to 150 μm, preferably within the range from 1 to 100 μm, preferably from 1 to 50 μm and preferably from 1 to 30 μm.

Within the meaning of the invention, D50 corresponds to the volume-average size, that is to say the value of the particle size which divides the population of particles examined exactly into two. The D50 is measured according to standard ISO 9276-Parts 1 to 6: "Representation of results of particle size analysis".

Advantageously, in the method of the invention, the medium acceptable in cosmetics, in perfumery and/or in pharmaceuticals comprises an aqueous phase (or a polar solvent, preferably a protic polar solvent) comprising at least 50% of water with regard to the weight of aqueous phase and/or an oily phase comprising at least 50% of organic solvent with regard to the weight of oily phase, said organic solvent being chosen from fatty esters, fatty alcohols, fatty acids and their mixtures.

According to an advantageous embodiment, the method of the invention comprises the following stages:
dissolving the COPA in the oily phase;
emulsifying the COPA solution obtained in the aqueous phase comprising at least one surfactant, preferably chosen from anionic surfactants and nonionic surfactants.

According to a preferred embodiment, the method of the invention comprises a stage consisting in dispersing COPA with a melting point M.p. in the aqueous phase comprising at least one basic compound and/or one surfactant chosen from anionic surfactants and nonionic surfactants, at a temperature of greater than or equal to M.p., and with stirring at a shear rate sufficient for the D50 of the emulsified COPA drops to be within the range from 0.1 to 50 μm, preferably within the range from 0.1 to 20 μm, within the range from 0.1 to 10 μm.

Preferably, the COPA is incorporated according to the method of the invention, with stirring within the range from 100 to 15 000 revolutions per minute, preferably from 1000 rev/min to 12 000 rev/min and sometimes at more than 8000 rev/min. Use is made, for the low stirring speeds, for example, of a homogenizer, such as a deflocculator, whereas, for the stirring speeds of more than 8000 rev/min, a device of Ultra-Turrax type is used.

Advantageously, the method of the invention comprises the use of a COPA with predominantly acid (that is to say to more than 50% by weight acid) chain ends in a medium (preferably an aqueous medium) comprising a basic compound which reacts with the acid chain ends to give carboxylates, the latter acting as surfactant. Preferably, the ratio of the end carboxyl groups to the end amino groups of the COPA used in the present invention is within the range from 60/40 to 95/5.

The term "basic compound" is understood to mean an alkali metal hydroxide or an amino compound. Mention may be made, as examples, of sodium hydroxide or potassium hydroxide.

Preferably, the composition according to the invention comprises from 0.2 to 3.0 mol of basic compound per mole of end hydroxyl groups of the COPA.

Preferably, the COPA is dispersed in said medium (preferably said aqueous medium) at a temperature greater than or equal to the melting point M.p. of the COPA, preferably at a temperature within the range from 70 to 200° C., preferably from 90 to 190° C.

The aqueous dispersions of example 1 below are in accordance with these preferred parameters.

A further subject matter of the present invention is the use of a copolyamide (COPA) in the manufacture of a cosmetic, pharmaceutical or perfumery product, said COPA being incorporated in the form of a composition in accordance with the invention.

A subject matter of the present invention is in particular a composition according to the invention as defined above, said composition being a colored, colorless and/or transparent product chosen from the following products:
  makeup products for the human face and body, such as foundation, tinted cream, loose or compact powder, eyeshadow, mascara, eyeliner, lipstick or nail varnish;
  care products for the human face and body, such as cream, milk, lotion, mask, scrubber, cleansing and/or makeup-removing products, deodorants, antiperspirants, shaving products or hair-removing products;
  hair products such as shampoos, products for the shaping of the hair, products for retaining the hairstyle, anti-dandruff products, products for combating hair loss, products for combating dryness of the hair, hair dyes or bleaching products;
  perfumery products, such as fragrance, milk, cream, or loose or compact scented powder.

EXAMPLES

The following examples illustrate the present invention without limiting the scope thereof. Unless otherwise indicated, all of the percentages are by weight.

Example 1

COPAs Used:
  COPA 1: copolyamide Pip.10/12 with a ratio of 72/28 (percentage by weight), "Pip" being piperazine.
  COPA 2: copolyamide 6/6.6/12 with a ratio of 35/20/45 (percentage by weight).
An aqueous dispersion of COPA 1 and then of COPA 2 are manufactured according to the same following method:
  15% by weight of COPA are added to water (84%) mixed with 1% of NaOH, with stirring (300 rev/min) and at a temperature maintained above the melting point of the COPA, in this instance maintained at 150° C., and the combination is homogenized until an aqueous dispersion of COPA particles with a D50 within the range from 0.5 to 5 µm is obtained; then
  the dispersion is allowed to cool to ambient temperature (25° C.)

An aqueous dispersion of COPA 1 and an aqueous dispersion of COPA 2 (compositions according to the invention) are respectively obtained in example 1 and can advantageously be incorporated in a cosmetic formulation as in the following examples:

Example 2

Cream Formulation:

|  | Cream | % |
| --- | --- | --- |
| phase A (oily) | stearic acid | 12.5 |
|  | cetyl alcohol | 0.5 |
| phase B (aqueous) | triethylamine | 2 |
|  | glycerin | 10 |
|  | COPA 1 dispersion of example 1 | 7 |
|  | water | q.s. for 100 |
|  | preservative (Germall plus) | 0.1 |

Procedure:
  A and B are separately heated to a temperature of approximately 90° C.;
  B is poured into A, with stirring (using a deflocculator of Silverson® homogenizer type) for at least 5 minutes and until a homogeneous emulsion is obtained;
  slow stirring is continued, while gradually lowering the temperature to 30° C., and the preservative is added.

A protective white cream is obtained which has a "smooth" appearance when being taken up and applied.

Example 3

Makeup-Removing Milk Formulation:

|  | Makeup-removing milk | % |
| --- | --- | --- |
| phase A (oily) | stearic acid | 3.5 |
|  | liquid paraffin | 9 |
|  | cetyl alcohol | 0.9 |
|  | PEG monostearate (Tefose 1500) | 0.9 |
| phase B (aqueous) | triethylamine | 1.8 |
|  | water | q.s. for 100 |
|  | COPA 2 dispersion of example 1 | 5 |
|  | water | q.s. for 100 |
|  | preservative (Phenonip) | 0.2 |

Procedure:
  A and B are separately heated to 80° C.;
  B is poured slowly into A, with stirring (with a deflocculator) for at least 5 minutes and until a homogeneous emulsion is obtained;
  slow stirring is continued, while gradually lowering the temperature to 30° C., and the preservative is added.

A fluid makeup-removing milk is obtained which, applied to the skin, effectively absorbs the impurities (makeup, excess sebum) from the skin.

Example 4

O/W Mascara Formulation:

|  | O/W mascara | % |
| --- | --- | --- |
| phase A (oily) | beeswax | 5 |
|  | ozokerite | 7 |
|  | carnauba wax | 3 |
|  | stearic acid | 5 |
|  | glyceryl stearate | 5 |
|  | Sepicide | 0.5 |
| phase B (aqueous) | water | q.s. for 100 |
|  | triethylamine | 1.5 |
|  | propylene glycol | 5 |
|  | black iron oxide | 10 |
|  | COPA 1 dispersion of example 1 | 7.5 |
| active agent | water | 1 |
|  | D-panthenol | 0.5 |

Procedure:
  the oily phase is heated to 90° C.;
  the pigment (black iron oxide) is dispersed under cold conditions using an Ultra-Turrax in the water with the propylene glycol and the triethylamine;
  the aqueous phase thus obtained is heated to 90° C. and the aqueous dispersion of COPA 1 of example 1 is added thereto;
  the aqueous phase B is poured into the oily phase A with rapid stirring (200 rev/min) using a deflocculator over 5 minutes;
  the emulsion obtained is cooled with moderate stirring down to a temperature of 25-30° C. and then the active agent is added.

A mascara is obtained which curves the eyelashes in a "flexible" manner. The composition according to the invention provides a film-forming, sheathing and smooth curving effect for the eyelashes.

The invention claimed is:

1. A composition comprising:
   from 0.1 to 30% by weight of a copolyamide (COPA) comprising predominantly acid chain ends; and having a melting point ($T_m$) of 100°-130° C., and
   from 70 to 99.9% by weight of a medium acceptable in cosmetics, in perfumery and/or in pharmaceuticals, said medium comprising
   a basic compound,
   from 40 to 99.9% of oily phase comprising at least 50% of organic solvent that is fatty esters, fatty alcohols, fatty acids or their mixtures,
   from 0 to 30% of surfactant,
   with regard to the total weight of the composition.

2. The composition as claimed in claim 1, in which said medium comprises at least one of water, alcohols, alcoholic solutions, lipid compounds, glucide compounds, hydrocarbons, synthetic polymers, natural polymers and/or plant extracts.

3. The composition as claimed in claim 1, said composition having at least one of the following forms: dispersion, solution, emulsion, microemulsion, nanoemulsion, dry emulsion, suspension, aerosol, gel, compact gel, gum, plastic gum, paste, foam, cream, powder, loose powder, compact powder, expanded powder, butter, film, elastic film or their mixtures.

4. The composition as claimed in claim 1, in which said medium comprises an aqueous phase comprising at least 50% water.

5. The composition as claimed in claim 1, in which said medium comprises from 0.1 to 30% by weight of surfactant with regard to the total weight of COPA.

6. The composition as claimed in claim 1, comprising from 0.2 to 3.0 mol of basic compound per mole of end carboxyl groups of the COPA.

7. The composition as claimed in claim 4, comprising:
   from 0.1 to 30% of COPA,
   from 40 to 99.9% of oily phase and/or of aqueous phase,
   from 0.1 to 20% of surfactant,
   with regard to the total weight of the composition.

8. The composition as claimed in claim 1, additionally comprising a thickener.

9. The composition as claimed in claim 1, forming a dispersion of COPA dissolved in an oily phase dispersed in an aqueous phase in the presence of a surfactant.

10. The composition as claimed in claim 1, forming a dispersion of COPA dissolved in an aqueous phase dispersed in an oily phase in the presence of a surfactant.

11. The composition as claimed in claim 1, wherein the basic compound is an alkali metal hydroxide or an amino compound.

12. The composition as claimed in claim 1, said composition being a colored, colorless and/or transparent product:
   makeup products for the human face and body,
   care products for the human face and body,
   hair products,
   or perfumery products.

13. The composition as claimed in claim 5, wherein the surfactant is at least one anionic or non-ionic surfactant.

14. The composition as claimed in claim 13, wherein the surfactant is a salt of alkyl ether sulfate or of polyoxyalkylene, a dialkyl sulfosuccinate salt, a fatty acid salt or a copolyamide of ethylene oxide/propylene oxide, or their mixtures.

15. The composition as claimed in claim 12, that is
   foundation, tinted cream, loose or compact powder, eyeshadow, mascara, eyeliner, lipstick or nail varnish;
   cream, milk, lotion, mask, scrubber, cleansing and/or makeup-removing products, deodorants, antiperspirants, shaving products or hair-removing products;
   shampoos, products for the shaping of the hair, products for retaining the hairstyle, antidandruff products, products for combating hair loss, products for combating dryness of the hair, hair dyes or bleaching products; or
   fragrance, milk, cream, or loose or compact scented powder.

16. A composition comprising:
   from 0.1 to 30% by weight of a copolyamide (COPA) comprising predominantly acid chain ends, and having a melting point (Tm) of 100°-130° C., and
   from 70 to 99.9% by weight of a medium acceptable in cosmetics, in perfumery and/or in pharmaceuticals, said medium comprising
   a basic compound;
   from 40 to 99.9% of oily phase and of aqueous phase, said aqueous phase comprising at least 50% water and an oily phase comprising at least 50% of organic solvent that is fatty esters, fatty alcohols, fatty acids or their mixtures
   from 0 to 30% of surfactant,
   at least one of water, alcohols, alcoholic solutions, lipid compounds, glucide compounds, hydrocarbons, synthetic polymers, natural polymers and/or plant extracts
   with regard to the total weight of the composition,
   said composition having at least one of the following forms: dispersion, solution, emulsion, microemulsion, nanoemulsion, dry emulsion, suspension, aerosol, gel, compact gel, gum, plastic gum, paste, foam, cream, powder, loose powder, compact powder, expanded powder, butter, film, elastic film or their mixtures.

* * * * *